United States Patent
Saghai Maroof et al.

(10) Patent No.: US 8,003,856 B2
(45) Date of Patent: Aug. 23, 2011

(54) LOW PHYTIC ACID, LOW STACHYOSE, HIGH SUCROSE SOYBEAN LINES

(75) Inventors: Mohammad A. Saghai Maroof, Blacksburg, VA (US); Glenn R. Buss, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 630 days.

(21) Appl. No.: 12/033,830

(22) Filed: Feb. 19, 2008

(65) Prior Publication Data

US 2008/0199591 A1 Aug. 21, 2008

Related U.S. Application Data

(60) Provisional application No. 60/890,426, filed on Feb. 16, 2007, provisional application No. 60/890,471, filed on Feb. 17, 2007.

(51) Int. Cl.
*A01H 5/00* (2006.01)
*A01H 1/00* (2006.01)
(52) U.S. Cl. ......... 800/312; 800/260; 800/263; 800/298
(58) Field of Classification Search .................. None
See application file for complete search history.

(56) References Cited

U.S. PATENT DOCUMENTS

| | | |
|---|---|---|
| 5,710,365 A | 1/1998 | Kerr et al. |
| 6,147,193 A | 11/2000 | Kerr et al. |
| 6,653,451 B1 | 11/2003 | Kerr et al. |

OTHER PUBLICATIONS

Hitz et al. Biochemical and molecular characterization of a mutation that confers a decreased raffinosaccharide and phytic acid phenotype on soybean seeds. (2002) Plant Physiology; vol. 128; pp. 650-660.*
Chappell, A.S. et al., Plant Breeding 125:493-500,2006.
Gao, Y. et a., Crop Sci. 47:1797-1803, 2007.
Hegeman, C.E. et al., Plant Physiology 125:1941-1948, 2001.
Hitz, W.D. et al., Plant Physiology 128:650-660, 2002.
Walker, D.R. et al., Crop Sci. 45:390-397, 2006.
Wilcox, J.R. et al., Crop Sci. 40:1601-1605, 2000.
Yuan, F.-J. et al., Theor. Appl. Genet. 115:945-957, 2007.

* cited by examiner

*Primary Examiner* — Cathy Kingdon Worley
(74) *Attorney, Agent, or Firm* — New River Valley IP Law; Michele L. Mayberry

(57) ABSTRACT

The present invention provides novel soybean lines having high sucrose content and low phytic acid and low stachyose content. The soybeans are easily digested and provide high energy content for animals and humans. The low phytic acid content permits animal feed to be produced that does not require phytase, yet does not result in significant production of pollution to the environment from excretion by farm animals.

16 Claims, No Drawings

SEQUENCE LISTING

```
<160> NUMBER OF SEQ ID NOS: 9

<210> SEQ ID NO 1
<211> LENGTH: 20
<212> TYPE: DNA
<213> ORGANISM: Soy Bean

<400> SEQUENCE: 1
cagcaatgcc atcctctatg                                          20

<210> SEQ ID NO 2
<211> LENGTH: 20
<212> TYPE: DNA
<213> ORGANISM: Soy Bean

<400> SEQUENCE: 2
gaatcctcgc atgtgttgtg                                          20

<210> SEQ ID NO 3
<211> LENGTH: 780
<212> TYPE: DNA
<213> ORGANISM: Soy Bean

<400> SEQUENCE: 3
tggattttat actaatgtca tatcattggt gttattttta ctagcactat ctatcctttg    60
catgctttgt ttaaaattta tgcattgtgc taattttata tggcaaaaat ggagaaacga   120
gttgattttt tcaaatgttc tgttgatgat tggcagccaa catctatagt cagttacaac   180
catctgggaa acaatgatgg tatgaatctt tcggctccac aaactttccg ttccaaggaa   240
atctccaaga gcaacgttgt tgatgatatg gtcaacagca atgccatcct ctatgagcct   300
ggtgaacatc cagaccatgt tgttgttatt aaggtaaatt ttgtttcacc cattttctg   360 tttctttctc ttgtcagggc tttgattatt ctatctgctt tgttgccttt gcagtatgtg   420
ccttacgtag gggacagcaa gagagccatg gatgagtaca cttcagagat attcatgggt   480
ggaaagagca ccattgtttt gcacaacaca tgcgaggatt ccctcttagc tgctcctatt   540
atcttggact tggtccttct tgctgagctc agcactagaa tcgagtttaa agctgaaaat   600
gaggtctgta tgcattgcta aataatttca ttgcttgatt gtattagtca ttgtatttt   660 ttcagccttc tgaggtcact atgttgtggt gattgctgca gggaaaattc cactcattcc   720
acccagttgc taccatcctc agctacctca ccaaggctcc tctggtgagt ttaatctaat   780
```

-continued

```
<210> SEQ ID NO 4
<211> LENGTH: 25
<212> TYPE: DNA
<213> ORGANISM: Soy Bean

<400> SEQUENCE: 4
aggggacagc aatagagcca tggat                                              25

<210> SEQ ID NO 5
<211> LENGTH: 25
<212> TYPE: DNA
<213> ORGANISM: Soy Bean

<400> SEQUENCE: 5
aggggacagc aagagagcca tggat                                              25

<210> SEQ ID NO 6
<211> LENGTH: 22
<212> TYPE: DNA
<213> ORGANISM: Soy Bean

<400> SEQUENCE: 6
cctggtgaac atccagacca tg                                                 22

<210> SEQ ID NO 7
<211> LENGTH: 22
<212> TYPE: DNA
<213> ORGANISM: Soy Bean

<400> SEQUENCE: 7
cctggtgaac atccagacga tg                                                 22

<210> SEQ ID NO 8
<211> LENGTH: 13
<212> TYPE: PRT
<213> ORGANISM: Soy Bean

<400> SEQUENCE: 8

Pro Gly Glu His Pro Asp His Val Val Val Ile Lys Val
1               5                   10

<210> SEQ ID NO 9
<211> LENGTH: 13
<212> TYPE: PRT
<213> ORGANISM: Soy Bean

<400> SEQUENCE: 9

Pro Gly Glu His Pro Asp Asp Val Val Val Ile Lys Val
1               5                   10
```

LOW PHYTIC ACID, LOW STACHYOSE, HIGH SUCROSE SOYBEAN LINES

CROSS-REFERENCE TO RELATED APPLICATIONS

This application relies on the disclosure of, and claims the benefit of the filing date of, U.S. provisional patent application No. 60/890,426, filed 16 Feb. 2007, and U.S. provisional patent application No. 60/890,471, filed 17 Feb. 2007, the entire disclosures of both of which are hereby incorporated herein by reference.

BACKGROUND OF THE INVENTION

1. Field of the Invention

The present invention relates to the field of agriculture and crop sciences. More specifically, the invention relates to soybean lines that have been developed to have beneficial traits, including, but not necessarily limited to, low phytic acid content, low stachyose content, and high sucrose content.

2. Description of Related Art

The field of crop science involves, at least to some extent, developing new and improved crop plants that have beneficial characteristics. Those characteristics can be any of interest to those in the agriculture industry, but typically relate to disease or pest resistance, extreme water condition (e.g., drought, flood) tolerance, and improved nutritional value for animals and humans. Great effort and funding is expended in developing these new crops. Traditional development techniques include crossing of strains of a crop, and screening progeny for the presence or absence of a trait of interest. Newer methods include genetic engineering of plants by intentional insertion or deletion of genes known to be involved in particular biochemical pathways of interest.

Soybeans have traditionally been a staple of the diets of many cultures throughout the world. Increasingly, soybeans have become an important part of the diets of residents of the U.S. as well. Furthermore, soybeans are a major source of material for animal feed, particularly in the agricultural raising of animals for human consumption. Accordingly, an increasing number of studies have been instigated in the last twenty years to understand the biochemistry and genetics of soybeans and to develop improved strains of soybeans for human, and to some extent animal, consumption. Other studies have focused on improving the nutritional value of other plants that serve as a food source for animals and humans.

Soybeans contain several beneficial traits that make them advantageous as a food source for animals and humans. For example, soybeans are relatively high in protein content (about 40% by dry weight), relatively high in oil (about 21% by dry weight), and relatively high in soluble carbohydrate (e.g., sugar) content (about 11% by dry weight). Soybeans also contain useful amounts of phosphorus; however, much of the phosphorus exists in a form that is not directly available to animals and humans. Although soybeans are an excellent source of food for animals and humans, it has been recognized by the inventors that the nutritional value of soybeans can be increased by improvement of certain traits. Among those traits are available phosphorus content and available sugar content.

Phytic acid, or myo-inositol (1,2,3,4,5,6) hexakisphosphate, (also referred to as phytate when in its salt form) is typically the main form of phosphorus in plant seeds, including soybean seeds. It serves as a storage form for phosphate, and can be present in seeds at amounts exceeding 65% of total phosphorus. However, phytic acid is not highly digestible by animals and humans, and can actually decrease the nutritional value of the seeds by chelating nutritionally important minerals, such as calcium, zinc, magnesium, and iron, rendering those minerals unavailable for use by animals and plants consuming the seeds. To overcome this negative trait of seeds and provide a usable source of phosphorus for animals and humans, soybean food products are typically supplemented with either inorganic phosphate or the enzyme phytase (which catalyzes the breakdown of phytate). The addition of the enzyme phytase is costly and cumbersome, increasing the cost of production of food products. Furthermore, addition of inorganic phosphate raises the total phosphorus content of the food products, resulting in excess phosphate being ingested and ultimately excreted by the animal or human. In agricultural settings, the excreted phosphate becomes a pollutant to the environment, harming agricultural land and waterways that accept run-off from the agricultural land.

Stachyose is a significant form of soluble carbohydrate in seeds as well. However, stachyose is not digestible by monogastric animals, including humans and many agriculturally important animals, because these animals lack the enzyme a-galactosidase. The inability of these animals and humans to digest this sugar results not only in a waste of energy available from the seeds, but also can result in digestive problems for the human or animal consuming the seeds or products produced from the seeds. Thus, the inventors have recognized that development of a line of plants, such as soybean plants, having low stachyose content would improve the economic value of the plants as a food source.

It has been known in the art for over thirty years that expression of certain agriculturally relevant traits of soybeans are linked. For example, sucrose content of soybeans is known to be positively correlated with raffinose content and negatively correlated with stachyose content. Further, and not surprisingly, stachyose content is known to be negatively correlated with raffinose content. Soybeans are considered to behave like diploid organisms for most traits. They have been characterized as having 20 different chromosomes, and are thus typically regarded as having 40 chromosomes in the diploid state. Twenty molecular linkage groups (designated as A1, A2, B1, B2, C1, C2, D1a, D1b, D2, E, F, G, H, I, J, K, L, M, N, and O) have been identified in soybeans, which probably correspond to the 20 haploid chromosomes A1, A2, B1, B2, C1, C2, D1a, D1b, D2, E, F, G, H, I, J, K, L, M, N, and O.

Linkage of traits in soybeans, as in any other organism, can be considered from two different perspectives: physical linkage of genes in the genome, and expression of disparately located genes by way of similar expression control elements. For the purposes of traditional development or engineering of new and improved strains, the physical linking of genes is a key consideration. Using traditional development strategies, various traits are segregated based on the frequency of crossing-over events during generation of germ cells. In general, the closer two genes are to each other on the genome, the less likely they are to be separated by a crossing-over event. Statistical analyses can be performed, and values assigned to gene (trait) pairs, to give crop scientists an idea of how close two genes are on a chromosome, and thus how likely they are to co-segregate (i.e., how closely they are linked).

Numerous studies have been performed, and improved soybean lines developed over the years. For example, U.S. Pat. Nos. 6,653,451, 6,147,193, and 5,710,365 to DuPont/Pioneer, and a publication by Hitz et al. (Hitz, W. D. et al., 2002, Plant Physiology 128:650-660) disclose various improved soybean strains. Further, Wilcox et al. (2000) disclose the identification of mutations resulting in low phytic acid content in soybeans. These mutations were mapped by Walker et al. (Walker, D. R. et al., 2006, Crop Sci. 45:390-397) to linkage groups (LG) N at a locus near marker Satt237, and LG L at a locus near Satt527. Each of these references is hereby incorporated into this disclosure in its entirety by reference.

Although much research has been performed, and numerous improved soybean lines have been developed, the inventors have recognized that there still exists a need in the art for new, improved soybean lines that have beneficial characteristics. In particular, the inventors have realized that new soybean lines are needed that provide nutritional characteristics that are different and/or improved as compared to soybean lines now known in the art.

SUMMARY OF THE INVENTION

The present invention addresses needs in the art by providing a new soybean strain or line having beneficial nutritional traits. In general, the soybeans of the invention are seeds that are low in stachyose content and low in phytic acid content. In addition, they can be high in sucrose content. The soybeans of the invention differ in genetic make-up from other soybeans having similar characteristics, and thus constitute novel biological material. The soybean strains according to the present invention comprise one or more genes encoding proteins involved in the biochemical pathways of stachyose and phytic acid production, where the genes are different in nucleotide sequence than other characterized genes known to be involved in these biochemical pathways, have one or more mutations in controlling regions of such genes, or lack one or more such genes. The expression of the gene(s), the activity of the encoded proteins, or both, is thus altered as compared to corresponding wild-type soybeans and other known soybeans having mutations affecting phytate, stachyose, and/or sucrose amounts in soybean seeds. The genetic alterations of the strains of the invention thus may be in the coding portion of the genes or may be in the regulatory elements of the genes.

In another aspect, the invention provides progeny derived from the mutants of the invention. In essence, the progeny are encompassed by the description of a soybean strain or line of the invention; however, it is to be recognized that the phenotypic traits of the soybean lines or strains of the invention are heritable traits, and thus can be passed on to progeny, either by way of continuous propagation of the soybean lines or by way of crosses with other soybean strains. Progeny may thus have one or more different traits than the parental strains, while still being encompassed by the present invention.

In an additional aspect, soybean plants are provided. Soybean plants are plants grown from the soybeans of the invention, and are capable of producing seeds having the heritable traits of the soybeans of the invention. In addition to use as a means for producing soybeans according to the invention, the plants may find uses in agriculture in general, for example as a means for introducing nitrogen into the soil, as a research crop for genetic analysis of soybean traits, etc. Of course, progeny of the plants are encompassed by the invention as well.

In a further aspect, the present invention provides consumable products comprising the soybeans of the invention or material made from the soybeans of the invention. In general, the consumable products are those suitable for ingestion, consumption, etc. by animals and humans. Preferably, the consumable products are relatively easy to digest, enhance metabolizable energy, and result in reduced excretion of phytic acid or salts thereof. Furthermore, the consumable products, in embodiments, are characterized by the absence of phytase or high levels of inorganic phosphate not naturally present in the soybeans. For example, the consumable product may be soy meal for use as or in animal feed, which does not contain added phytase or inorganic phosphate. The consumable products may be in a form typically used directly as a food product for animals and humans, or may be in a form typically used as an additive or precursor to a food product that is ultimately used as a food.

In yet another aspect, the invention provides a method of producing a soybean strain having seeds with low phytate and low stachyose content, and, optionally, high sucrose content. In general, the method comprises crossing a low phytate, low stachyose strain according to the invention with another strain of soybean. The method can further comprise harvesting seed from the cross, and, optionally, propagating the resulting strain for one or more generations. Where desired, the method may include assaying the strain for one or more characteristics of interest, such as seed content of phytic acid, stachyose, and sucrose.

In yet an additional aspect, the invention provides a method of improving the nutritional value of a soybean. In general, the method comprises creating a soybean having the seed characteristics of low phytate level, low stachyose level, high sucrose level, or a combination of two or all three of these. In related aspects, the invention provides methods of improving the nutritional value of foods that contain soybeans or soybean products, where the methods include using a soybean line of the present invention to produce the food; methods of improving the efficiency of raising agricultural animals that are fed food containing soybeans or soybean products, where the methods include using a soybean line of the present invention to produce the food and feeding the food to the animals; and methods of reducing environmental pollution as a result of farming, where the methods include feeding agricultural animals food containing soybeans or soybean products that contain low levels or no added phytase and/or inorganic phosphorus.

In yet a further aspect, the invention provides a method for determining phytate content of a sample. In general, the method comprises acidic extraction of samples; salting out of substances; diluting soluble components; addition of Wade's Reagent; and determining phytate content using a calorimetric method. Phytate content determined by this method is comparable to other techniques known in the art over a wide range of concentrations. However, the present method is simpler and less expensive than other methods known in the art.

DETAILED DESCRIPTION OF VARIOUS EMBODIMENTS OF THE INVENTION

Reference will now be made in detail to various exemplary embodiments of the invention. It is to be understood that the following detailed description is not a limitation on the invention, but rather is provided to assist in explaining certain features and embodiments of the invention.

In a first aspect, the invention provides novel soybean lines. In general, the soybeans of the invention have at least the following heritable traits: seeds having low stachyose content and low phytic acid content. In preferred embodiments, the soybean lines also have the heritable trait of seeds having high sucrose content. As used herein, the term "soybean" describes members of the species *Glycine max* L. Merr., including all sub-species, strains, lines, etc. In addition, as used herein, a soybean seed having "low" stachyose content is one having a stachyose content (dry weight) of 1% or less, including, but not limited to, 0.9%, 0.8%, 0.5%, 0.4%, 0.25%, 0.1%, or less, as measured using techniques known in the art. Undetectable amounts of stachyose are thus included within the range of "low" stachyose content. Further, as used herein, a soybean seed having "low" phytic acid content is one having a phytic acid content (dry weight) of 13 mg or less of phytate per gram of seed, such as 12 mg/g, 10 mg/g, 9.5 mg/g, 5 mg/g, 2.5 mg/g, or less, as measured using techniques known in the art. Undetectable amounts of phytic acid are thus included within the range of "low" phytic acid content. In addition, as used herein, "high" levels of sucrose are amounts at or above 7% (dry weight) of sucrose, such as 8%, 9.0%-9.5%, 11.0%-11.5%, 12.5%, and 14.5% or more. Of course, there is a natural limit to the amount of sucrose that may be contained in a viable seed, and the upper limit will be defined by that amount (which may vary from seed to seed based on the levels of other substances in the seed). Typically, the amount of sucrose will not exceed 15%, although this should not be considered as a strict upper limit.

It is to be noted at this point that the soybeans of the present invention are unique and thus different from soybean lines characterized and known in the art prior to this disclosure. The soybean lines (and plants, lines, products, etc. derived therefrom) of the invention thus exclude other soybean lines known in the art, which are disclosed as having similar or overlapping phenotypic characteristics. Thus, strains not encompassed by the invention include those discussed by Walker et al., Hitz et al., and in U.S. Pat. Nos. 5,710,365, 6,147,193, and 6,653,451, including, but not necessarily limited to strains CX1834-1-2, LR28, LR33, LR28/33, M776, LR3705, and LR4271.

In a preferred embodiment, the soybean line of the invention is a line referred to herein as V99-5089, which shows the heritable traits of: seeds having low phytate, low stachyose, and high sucrose content. As discussed in more detail below, the V99-5089 strain has been characterized as being distinct from characterized strains known in the art, and thus is a novel strain having useful characteristics. Genetic changes within the V99-5089 strain map to loci that are different from loci of strains characterized in the art, and thus represent different genetic changes.

In another preferred embodiment of this aspect of the invention, soybeans are provided that comprise the genetic locus or loci of strain V99-5089 that are responsible for the seed characteristics of low phytate content, low stachyose content, or both. Often it is further preferred that the soybeans comprise the genetic locus of strain V99-5089 that is responsible for the seed characteristic of high sucrose content. These loci, independently or in any combination, may be present in strain V99-5089 or any other soybean, and may be introduced into other soybeans by way of intentional crossing of two strains to incorporate the desired traits into progeny, or by way of genetic engineering techniques or any other techniques (e.g., mutagenesis of wild type soybeans). As plant breeding techniques are known and well established, it is envisioned that controlled crossing of strains (with or without the use of DNA extraction and marker-assisted selection approaches) will typically be used to move the desired loci into desired soybeans.

A preferred characteristic of soybeans according to the present invention is acceptable germination rates. It has been reported that soybean seeds having low phytate content have reduced ability to germinate, and are thus inappropriate for seed stock and use in production of commercial quantities of beans. According to a preferred embodiment of the present invention, soybeans having the traits of low phytate, low stachyose, and/or high sucrose also have commercially acceptable rates of germination, and thus are suitable for use in commercial ventures, such as in commercial farming. Yet further, the strains of the invention preferably show acceptable production of various sugars, polysaccharides, and oils, at levels desirable for agricultural use and use in production of oils and foods for human consumption.

In another aspect, the invention provides progeny of the soybean strains of the invention. Progeny according to the invention are soybeans (lines, strains, etc.) derived through breeding (with or without marker-assisted selection) to a soybean having the heritable seed characteristics of low phytate, low stachyose, and preferably high sucrose content. Progeny thus may contain one, two, or all three of the recited heritable characteristics of a soybean strain of the present invention, and preferably show at least the low phytate and/or low stachyose characteristics. As is understood in the art, progeny may represent a cross between two strains having different characteristics, with the goal of creating a strain having desirable characteristics from each strain. According to the invention, the term progeny includes all such crosses and resulting strains where the genetic loci for the seed characteristics of low phytate, low stachyose, and/or high sucrose are present. Preferably, these characteristics can be identified as originating from a preferred strain of the invention, such as strain V99-5089 or its derivatives. In accordance with the discussion above, preferably, progeny according to the invention have acceptable germination rates and other commercially advantageous characteristics. For example, progeny of exemplary strain V99-5089 having improved germination rates, extended seed shelf-life, resistance to one or more herbicides, resistance to one or more insects, or other commercially advantageous characteristics are envisioned by the invention.

The invention also provides soybean plants. While the term soybean as used herein broadly encompasses all parts and life stages of the soybean plant, it should be clear that soybean seeds, soybean plants in general, and different parts of soybean plants can have different uses, functions, and genetic complements. Thus, in embodiments of the invention, soybean plants and portions of plants (e.g., plant tissues) are provided. In general, soybean plants find use as a source for genetic material for creation of progeny. However, other uses include, but are not limited to, plant parts, such as leaves and flowers, which can be used for genetic analysis of the plant in its polyploid, diploid, or haploid state. Additional uses for soybean plants in general and portions thereof include use as a source for isolation of genetic material for cloning of genes or collections of genes, for metabolic engineering, for mapping of chromosomes or genes on chromosomes, and for analysis of biochemical pathways in certain plant tissues, to name a few. Plants according to the present invention can have any number of phenotypic characteristics in addition to the seed characteristics of low phytic acid, low stachyose, and optionally high sucrose. For example, the plants may have the characteristic of improved germination (as compared to other strains having a similar phenotypic make-up), resistance to one or more herbicides or insecticides, drought tolerance, insect resistance, or other commercially advantageous characteristics are envisioned by the invention. Of course, combinations of desirable characteristics may exist in a plant.

In exemplary embodiments, soybean plants of the invention are used for commercial production of soybeans. Typically, the soybeans are grown in commercial size fields for harvest and use in animal feed and human food production, but can also be used for biofuel production. Soybean plants of the invention preferably have germination rates similar to other commercial varieties of soybean, and produce beans at a commercially acceptable level. In some embodiments, soybean plants of the invention are used for development of new strains of soybeans. Such a use can be a commercial use to develop new useful strains of soybean, or a research use to characterize phenotypic and genotypic traits of soybeans. In yet other embodiments, soybean plants of the invention are used for research purposes to determine phenotypic or genotypic characteristics.

The soybean plants of the invention are, in preferred embodiments, plants of the V99-5089 strain or progeny thereof. In certain preferred embodiments, the soybean plants of the invention comprise the genetic loci of strain V99-5089 that are responsible for the seed characteristics of low phytate content and low stachyose content. In some embodiments, the soybean plants also comprise the genetic locus of V99-5089 responsible for the seed characteristic of high sucrose content.

As should be evident from the disclosure above, the soybeans of the invention can be used in any way that is known for soybeans in general. They thus may be used as a consumable product. Alternatively, they may be processed in one or more ways to produce a consumable product. Likewise, they may be used as grown or after processing as a component of a consumable product or as a biofuel. Further, they may be used for research purposes. In preferred embodiments, the soybeans of the invention are used as, or as part of, a food product for animals. In other embodiments, the soybeans are used as, or as part of, a food product for humans. In preferred embodiments, the invention provides an improved soybean seed composition for human food and animal feed.

One particular use for the soybeans of the invention is as a component of animal feed. For example, the soybeans may be processed into soy meal for use in animal feed. Due to the low concentrations of phytate in the resulting product, it is not necessary to include in the product a phytase (or very little phytase is required) to improve utilization of phytate phosphorus. More specifically, commercially used soybeans for animal feed contain relatively high amounts of phytic acid. This phytic acid is substantially not absorbed by animals ingesting the feed, and is thus excreted. Excretion of this compound leads to high quantities of phytate or phosphorus in the environment, which has adverse effects on the environment, such as pollution of streams and other bodies of water. Alternatively, feed makers must add phytase to the feed/meal to provide an enzyme for breakdown of the phytic acid. Addition of the enzyme leads to a substantial increase in the cost of the feed as well as an increase in the complexity of production of the feed. The present soybean lines allow for feed that contains little or no phytase, and thus is cheaper and easier to make and store. Furthermore, because the preferred soybeans of the present invention are high in sucrose content, they are sweeter in taste. Accordingly, animals (and humans) find them more palatable and are more likely to consume them, particularly in amounts of nutritional importance. The soybeans thus provide a method of improving the health of animals (including humans) by providing soybeans that have a better taste than currently available soybeans without the characteristics of the present soybeans. Indeed, the soybeans of the present invention provide increased levels of energy, as compared to soybeans not having the present characteristics, in part due to the high concentrations of sucrose in the beans. Finally, because of the characteristics of the beans of the present invention, the beans are better tolerated by the digestive tracts of animals, and thus improve absorption of the nutrients of the beans by the animals and reduce the likelihood of feeding disruptions, particularly in animals in agricultural settings.

An additional use of the soybeans of the invention is as germ stock for developing strains of soybeans that have advantageous characteristics for growth in various localities. More specifically, different localities have different soil and weather conditions. Thus, certain strains or varieties of soybean grow and produce better in some localities as compared to others. The soybeans of the present invention contain stable, heritable genetic loci. Thus, the soybeans of the present invention can be used as germ stock for crossing with various other soybean strains to produce strains that are adapted for advantageous growth in a particular climate or growing conditions, while having the low phytic acid, low stachyose, high sucrose characteristic of the present strain.

In a further general aspect of the invention, consumable products comprising the soybeans of the invention or material made from the soybeans of the invention are provided. In general, the consumable products are those suitable for ingestion, consumption, etc. by animals and humans. Preferably, the consumable products are relatively easy to digest and result in reduced excretion of phytic acid or salts thereof. Numerous methods of making consumable products from soybeans are known, and any of such methods may be employed with the soybeans of the present invention. That is, the soybeans of the present invention behave in a similar fashion to currently available commercial strains, and no particular special treatment is required to use them in standard processing techniques.

Indeed, due to their particular genetic make-up, processing of soybeans according to the present invention can be simpler and more cost-effective than processing of presently available commercial soybeans. Due to the low levels of phytic acid in the soybeans, the consumable products can be characterized by the absence of phytase or inorganic phosphate not naturally present in the soybeans. For example, the consumable product may be soy meal for use as or in animal feed, which does not contain added phytase or inorganic phosphate. In preferred embodiments, the soybeans are strain V99-5089 or progeny thereof having the genetic loci responsible for low phytate, low stachyose, and/or high sucrose in seeds.

The food products according to the invention include, but are not limited to, soy meal for use in production of agricultural animal feed (e.g., swine feed, fowl feed), soy beans for use in agricultural animal feed, soy meal for use in human food, and soy beans for use in human food, and soy beans and meal for use in domesticated animal food (e.g., dog food). The form and ultimate consuming animal is not a critical consideration; thus, the food product may be in the form of a powder, granule, nugget, block, etc. Likewise, it may be produced in any size quantity, from micrograms to kilograms. The food product thus may comprise the soybeans or soybean products as the sole substance in the product, as a majority of the substances in the product (by weight or volume), or as a minority of the substances in the product.

Furthermore, the food products may comprise only a subset of the substances present in the soybeans of the present invention. For example, a food product may be made from the protein portion of the soybeans of the present invention, the carbohydrate portion, or the protein and carbohydrate portion of the soybeans. Chemical analyses of soybeans and other food products is a well known art, and can be applied to determine the content of substances in particular foods, including the content prior to addition of a component of a food product to the product during preparation.

In yet another general aspect of the invention, a method of producing a soybean strain having seeds with low phytate and low stachyose content, and, optionally, high sucrose content, is provided. In general, the method comprises crossing a low phytate, low stachyose strain according to the invention with another strain of soybean. Such a cross will result in at least a portion of the progeny having seed characteristics of low phytate, low stachyose, and/or high sucrose. In preferred embodiments, at least a portion of the progeny of the cross will have both low seed phytate content and low seed stachyose content. In yet further preferred embodiments, either or both of these traits are combined with high seed sucrose content.

A soybean strain according to the invention may be crossed with any other suitable soybean strain to produce progeny having desired traits, including low phytate, low stachyose seed content. Results of crosses performed with other genetically characterized strains indicate that the phenotypic characteristics of low phytate and low stachyose are detectable as heritable traits. They are thus genetic in nature and each can be mapped to a particular locus on a chromosome. In a preferred embodiment, a soybean strain according to this aspect is strain V99-5089 or a progeny thereof having the genetic loci responsible for the seed characteristics of low phytate, low stachyose, and/or high sucrose. As with any soybean strain according to the invention, progeny strains developed through crosses can be homozygous or heterozygous with respect to each characteristic, and the status of each can be independent with respect to each of the others.

According to the method, seed from the crosses may be harvested. Harvested seed can be used for any suitable purpose, including, but not limited to, analysis for genetic make-up, planting for characterization of phenotypic characteristics, and production of food and food products. The method thus can further comprise propagating the strain resulting from the cross for one or more generations. Additionally, the resulting progeny may be crossed with a parental strain or another strain (e.g., one having one or more desirable qualities) to improve strain characteristics, to manipulate genetic make-up (e.g., create a strain that is homozygous at a particular locus), or for any other reason. Additional crosses and back-crosses can be performed on any number of progeny generations to achieve a desired quality or set of qualities.

Where desired, the method of making a soybean line may include assaying the resulting strain for one or more characteristics of interest, such as seed content of phytic acid, stachyose, and sucrose. The results of the assay(s) can assist the breeder in selecting a progeny strain for further analysis (for research purposes) or for planting or further development (for commercial purposes).

In yet an additional general aspect of the invention, a method of improving the nutritional value of a soybean is provided. In general, the method comprises creating a soybean having the seed characteristic of low phytate level, low stachyose level, high sucrose level, or a combination of two or all three of these. In a preferred embodiment, the soybean is strain V99-5089 or a progeny thereof. As discussed above, current commercially available soybean lines have seed levels of phytic acid and stachyose that are high, resulting in food products for animal and human consumption that contain significant amounts of phosphorus and carbohydrate that are unavailable for uptake by the animals and humans. Further, the effect of phytic acid might result in a net loss of minerals from animals and plants ingesting the soybeans and products, due to the chelating effect of phytic acid. The present soybeans, which have low phytic acid and low stachyose contents, improve the nutritional value of the soybeans, as compared to current commercially available soybeans, by reducing the amount of "inactive" phosphorus in the soybeans and by reducing the amount of indigestible carbohydrate. Typically, a reduction in the indigestible sugar stachyose is accompanied by an increase in the digestible sugar sucrose, thus providing a double benefit to the nutritional value of the soybeans. As mentioned above, reduction in phytic acid content concomitantly reduces the chelating effect on certain minerals, improving the nutritional value of the soybeans of the invention yet further.

The method of improving the nutritional value of soybeans has a direct effect on improving the nutritional value of soybean products. Soybeans can be ingested by animals and humans as a direct-source product. But, numerous food products contain soybeans and soybean by-products as a component. By improving the nutritional value of the soybeans, the present invention likewise improves the nutritional value of products containing the soybeans or substances derived from the soybeans. Thus, in embodiments, the method of improving the nutritional value of soybeans is a method of improving the nutritional value of foods that contain soybeans or soybean products. In such embodiments, the method further comprises creating a food or food product comprising the soybeans. Stated another way, in these embodiments the method can be a method of using the soybeans of the invention to produce a food having improved nutritional value, as compared to current commercial foods derived from or comprising soybeans. Thus, in embodiments, the method is a method of making a food product having improved nutritional value, where the method comprises obtaining soybeans having low seed content of phytic acid and stachyose, and making a food product from the soybeans or a portion of the soybeans.

Accordingly, the present invention provides food comprising soybeans or portions of soybeans, where the food has higher nutritional value than an equivalent food made from current commercially available soybeans. In general, the food according to the invention has a lower level of phosphorus present in a biochemically unavailable form, and a lower level of polysaccharides in a biochemically unavailable form, and in particular a lower level of stachyose. Preferably, the food has a higher level of sucrose, which is attractive as a taste and available as an energy source for the animal or human ingesting the food.

Another result of the improved soybean strains of the invention is the ability to provide a method of improving the efficiency of raising agricultural animals that are fed food containing soybeans or soybean products. In embodiments, this ability is reflected as a method of improving the health and/or diet of animals by feeding them food comprising or derived from soybeans of the present invention. It is to be noted that the same effect can be achieved in companion animals as well as humans who are fed food comprising the soybeans or products therefrom. According to the method, one can use a soybean of the present invention to produce the food or product, and feed the food to the animals (or humans). As compared to others fed a similar food, but made with current commercially available soybeans or products therefrom, those fed according to the present method will absorb an increased amount of digestible carbohydrate and will ingest a lower amount of indigestible phosphorus. Furthermore, loss of minerals due to the effect of phytic acid on the animal will be decreased. The net effect will be an improved diet, improved health of the animal or human, and (where it is applied to agricultural animals) an improvement in the cost-efficiency of raising the animal. It is to be noted again here that a reduction in phytic acid in the soybeans reduces the amount (and cost) of phytase or inorganic phosphate needed to create a food.

One additional advantage to be noted is that the method of the invention provides a reduction in environmental pollution as a result of farming. That is, because less phytic acid is consumed by agricultural animals, and because less inorganic phosphorus is added to the soy meal, less phosphorus is excreted by the agricultural animals, and a reduction in pollution of water and farm land occurs. According to this embodiment of the method, the method includes feeding agricultural animals food containing soybeans or soybean-derived products that contain low levels or no added phytase and/or inorganic phosphorus.

In yet a further general aspect, the invention provides a method for determining phytate content of a sample. In general, the method comprises acidic extraction of samples; salting out of substances; diluting soluble components; addition of Wade's Reagent; and determining phytate content using plasma emission spectroscopy (ICP). In an exemplary embodiment, the method comprises: grinding soybean seed; combining the ground seed with hydrochloric acid (HCl); mixing the combination continuously for at least 10 hours; centrifuging the mixture to separate out soluble from insoluble substances; and assaying for total phosphorus using a calorimetric assay based on the Wade Reagent method. Phytate content is thus measured as a function of total phosphate, assuming a 1:1 correlation between the two.

EXAMPLES

The present invention will now be further detailed with reference to data relating to an exemplary soybean strain according to the invention.

Example 1

A Colorimetric Method for Phytic Acid Analysis

Unless otherwise indicated, phytic acid content of soybeans was determined according to the method of Gao et al. (2006). Modifications to the assay can, of course, be made while still achieving similar results. For example, to achieve a 10% NaCl sample, one may add 1 g NaCl to a 10 ml crude extract sample, or may add a concentrated stock solution of NaCl to the sample (e.g., add 0.5 ml of 20% NaCl solution). Likewise, the sample volume may be reduced to any suitable volume (e.g., from 25 ml to 3 ml). Furthermore, the assay may be modified to work in a multi-sample fashion, such as in a 96-well plate for high through-put screening.

Example 2

Characterization of Soybean Line V99-5089

To address needs in the art for soybean lines having improved nutritional qualities, a line having seed content with low phytic acid and low stachyose and with high sucrose was developed. This line is referred to herein as V99-5089, and it was developed from a cross between V71-370 and PI 87013.

Materials and Methods for Mapping and QTL Analysis:
Sugar (sucrose, raffinose and stachyose) extraction for HPLC analysis: 0.9 to 1 g of ground powder of soybean seeds for each sample was used for sugar extraction. Chemical procedure and protocol details for HPLC analysis were as reported in Cicek et al., 2006.

DNA extraction: Plant tissue was collected in the field or greenhouse individually from F2 plants. Usually a top trifolio leaf was cut and placed into 2 ml microtubes and on dry ice. DNA was isolated from frozen soybean leafs using CTAB buffer and protocol described by Maroof et al., 1984. DNA integrity was evaluated by gel-electrophoresis in a 1% agarose and ethidium bromide staining.

PCR: Polymerase chain reactions for SSR assay were performed in a total volume of 10 ul in a GeneAmp PCR System 9700 (Applied Biosystems, Foster City, Calif., USA). Touchdown PCR profile was used for SSR amplification as follows: initial denaturing for 5 min at 95° C., followed by 2 cycles of 1 min at 95° C.-30 sec. at 51° C.-45 sec at 68° C.; 10 cycles of 1 min. at 95° C.-30 sec. at 49° C.-45 sec. at 68° C.; 30 cycles of 1 min 95° C.-45 sec. at 47° C.-45 sec. at 68° C., and then followed by a final extension for 8 min. at 68° C. PCR reaction procedure as well as polyacrylamide gel electrophoresis were conducted according to Maroof et al., 1994.

Data analysis: The computer program Mapmaker 3.0b (Lander et al., 1987) was used for genetic map construction. The Haldane centimorgan function was chosen with error detection on. Initial grouping of markers was performed at LOD 3.0 with a maximum distance of 50 cM. To determine the most probable marker order, three optional commands were used including "compare", "ripple", and "try".

V99-5089 was grown in a greenhouse and harvested for analysis of seed content. Seed was pooled and assayed for sucrose and stachyose content. The results showed that line V99-5089 had a seed content of sucrose ranging from 12.41 to 13.24% (dry weight) and a stachyose content ranging from 0.36 to 0.60% (dry weight). Additional analyses of a different planting showed that line V99-5089 has a seed content of sucrose of 10.79 to 11.57% (dry weight) and a seed content of stachyose ranging from 0.22 to 0.27% (dry weight). The line was thus a low stachyose line suitable for further characterization.

The V99-5089 line was analyzed for phosphorus content in seeds. Results of an analysis of four samples of line V99-5089 showed phytate phosphorus levels of 1.3-1.6 (mean=1.0) μg of phosphorus per gram dry weight of seed. At the same time, the line showed inorganic phosphorus levels of 23.9-28.2 (mean=26.0) μg of phosphorus per gram dry weight of seed. The V99-5089 line is thus a low phytic acid, high inorganic phosphorus line as well as being a low stachyose, high sucrose line.

Example 3

Creation of Progeny Strains Having Low Stachyose, Low Phytate Characteristics

To show that the low phytate, low stachyose traits are heritable, crosses were made between line V99-5089 and other soybean lines, and the progeny analyzed for seed content of these traits. Results show that both the low phytate and low stachyose traits are heritable. Thus, breeding programs can be developed to create new strains of soybean having these advantageous characteristics.

Table 1 depicts results of crosses of an exemplary soybean of the invention (V99-5089) with a common agricultural variety of soybean (Essex). As can be seen from the table, some progeny of this cross have both the low phytate, low stachyose phenotype. The progeny also show the trait of high sucrose content in seed. Furthermore, the progeny show reasonable yields (some up to 90% of the Essex parental strain). Thus, use of the soybeans of the invention as breeding stock is not only feasible, but can produce commercially valuable offspring. Table 1 also shows the importance of the developed stachyose marker (Satt453, which maps to linkage group B1) in classifying the F2-derived lines into high-(A) and low-(B) stachyose content groups.

TABLE 1

Agronomic and quality trait data on 40 F2-derived lines compared to their parents (ranked based on yield)

| ENTRY | NAME | Stach Type | Stach Marker | YIELD | MAT | HT | LOD | Germ | Suc | Raff | Stach | Phytate | Prot | Oil |
|---|---|---|---|---|---|---|---|---|---|---|---|---|---|---|
| 3 | Essex | P1 | A | 51.8 | 46.8 | 29.7 | 2.2 | 90.3 | 5.03 | 0.70 | 4.00 | 3890 | 42.45 | 18.04 |
| 27 | VO3-5764 | hi | A | 49.1 | 43.8 | 26.8 | 1.8 | 91.8 | 4.05 | 0.52 | 2.84 | 4351 | 43.09 | 18.26 |
| 36 | VO3-5782 | hi | A | 48.9 | 46.5 | 27.3 | 1.7 | 92.0 | 6.82 | 0.81 | 4.48 | 3932 | 42.38 | 17.32 |
| 1 | VO3-5712 | hi | A | 48.6 | 47.0 | 23.0 | 1.5 | 96.8 | 4.94 | 0.69 | 3.88 | 4114 | 42.56 | 18.04 |
| 28 | VO3-5766 | hi | A | 48.0 | 47.2 | 26.7 | 1.5 | 94.3 | 5.60 | 0.71 | 3.91 | 4392 | 42.70 | 16.79 |
| 31 | VO3-5772 | hi | A | 47.8 | 55.8 | 30.2 | 2.5 | 94.8 | 6.64 | 0.55 | 2.97 | 3674 | 42.97 | 17.58 |
| 42 | VO3-5794 | lo | B | 47.1 | 48.0 | 25.8 | 1.6 | 93.0 | 10.95 | 0.30 | 0.27 | 2762 | 44.01 | 16.98 |
| 22 | VO3-5754 | lo | B | 47.0 | 56.5 | 29.5 | 2.3 | 90.3 | 6.95 | 0.23 | 0.26 | 2960 | 44.33 | 16.50 |
| 40 | VO3-5790 | lo | B | 46.9 | 55.8 | 29.8 | 1.5 | 82.0 | 10.77 | 0.30 | 0.27 | 3278 | 43.75 | 16.50 |
| 39 | VO3-5788 | lo | B | 46.8 | 49.8 | 26.7 | 1.6 | 93.0 | 11.00 | 0.40 | 0.50 | 2926 | 42.01 | 18.14 |
| 8 | VO3-5726 | hi | A | 46.5 | 47.3 | 26.3 | 2.3 | 88.5 | 5.10 | 0.72 | 3.49 | 4265 | 44.07 | 17.19 |
| 19 | VO3-5748 | hi | A | 46.5 | 45.3 | 32.8 | 1.8 | 88.5 | 5.35 | 0.77 | 3.07 | 4450 | 43.64 | 18.37 |
| 33 | VO3-5776 | hi | A | 46.4 | 52.2 | 31.3 | 2.2 | 87.0 | 5.76 | 0.73 | 3.76 | 4155 | 42.83 | 17.35 |
| 35 | VO3-5780 | lo | B | 46.3 | 44.8 | 23.7 | 1.3 | 89.0 | 9.45 | 0.33 | 0.32 | 2935 | 43.41 | 17.31 |
| 30 | VO3-5770 | lo | B | 46.2 | 57.8 | 32.8 | 2.3 | 96.3 | 10.47 | 0.35 | 0.39 | 2929 | 43.18 | 16.24 |
| 24 | VO3-5758 | hi | A | 45.9 | 55.2 | 30.5 | 1.9 | 91.3 | 4.81 | 0.62 | 3.26 | 4432 | 43.68 | 16.89 |
| 37 | VO3-5764 | hi | A | 45.8 | 45.3 | 29.7 | 1.5 | 92.3 | 6.23 | 0.88 | 5.04 | 4172 | 42.97 | 17.41 |
| 26 | VO3-5762 | hi | A | 45.5 | 40.7 | 28.0 | 1.5 | 89.0 | 4.13 | 0.68 | 2.46 | 4405 | 42.68 | 17.25 |
| 14 | VO3-5738 | hi | A | 45.4 | 52.5 | 31.2 | 2.1 | 90.3 | 5.84 | 0.74 | 3.71 | 4414 | 43.48 | 17.10 |
| 4 | VO3-5718 | hi | A | 45.2 | 45.2 | 27.3 | 2.0 | 81.8 | 5.54 | 0.85 | 3.93 | 4124 | 44.58 | 17.18 |
| 16 | VO3-5742 | hi | A | 45.2 | 46.3 | 27.0 | 2.1 | 94.8 | 5.72 | 0.68 | 3.63 | 4043 | 45.52 | 17.65 |
| 41 | VO3-5792 | lo | B | 45.0 | 53.2 | 32.2 | 2.1 | 89.5 | 10.82 | 0.38 | 0.40 | 3452 | 41.80 | 17.56 |
| 21 | VO3-5752 | hi | A | 44.7 | 45.3 | 28.0 | 2.0 | 92.5 | 5.34 | 0.69 | 3.52 | 4316 | 42.74 | 18.06 |
| 38 | VO3-5786 | lo | B | 44.3 | 49.5 | 29.7 | 1.5 | 95.0 | 10.41 | 0.37 | 0.37 | 2939 | 44.49 | 15.71 |
| 7 | VO3-5724 | hi | A | 44.0 | 43.7 | 27.0 | 1.3 | 87.5 | 5.39 | 0.82 | 3.71 | 4543 | 42.52 | 17.17 |
| 32 | VO3-5774 | hi | A | 43.8 | 47.5 | 29.0 | 2.5 | 94.8 | 5.86 | 0.71 | 3.72 | 4852 | 42.59 | 16.74 |
| 11 | VO3-5732 | lo | B | 43.8 | 57.5 | 32.0 | 2.3 | 91.0 | 9.12 | 0.26 | 0.21 | 3063 | 42.34 | 17.25 |
| 20 | VO3-5760 | hi | A | 43.0 | 52.7 | 28.0 | 2.6 | 96.3 | 6.29 | 0.76 | 3.45 | 4269 | 44.39 | 17.16 |
| 23 | VO3-5756 | lo | B | 42.7 | 54.7 | 33.0 | 2.3 | 87.0 | 6.91 | 0.19 | 0.15 | 2941 | 43.38 | 17.05 |
| 25 | VO3-5760 | hi | A | 42.7 | 57.3 | 33.3 | 2.2 | 91.0 | 4.33 | 0.44 | 2.28 | 4556 | 42.31 | 17.47 |
| 29 | VO3-5768 | lo | B | 42.6 | 54.7 | 28.5 | 1.7 | 89.3 | 10.89 | 0.45 | 0.54 | 2862 | 40.29 | 16.83 |
| 6 | VO3-5722 | lo | B | 42.1 | 46.0 | 25.2 | 2.3 | 85.0 | 8.52 | 0.37 | 0.54 | 2962 | 44.00 | 17.02 |
| 5 | VO3-5720 | lo | B | 41.8 | 58.5 | 34.7 | 2.5 | 84.3 | 9.08 | 0.25 | 0.20 | 2778 | 43.85 | 17.00 |
| 12 | VO3-5734 | lo | B | 41.8 | 43.7 | 26.8 | 1.6 | 82.3 | 8.91 | 0.35 | 0.32 | 3019 | 43.61 | 17.27 |
| 9 | VO3-5728 | hi | A | 41.5 | 38.8 | 26.2 | 1.3 | 88.0 | 5.09 | 0.81 | 3.63 | 4369 | 42.77 | 17.95 |
| 13 | VO3-5736 | lo | B | 41.0 | 53.8 | 28.8 | 1.6 | 79.5 | 9.21 | 0.28 | 0.24 | 3224 | 42.73 | 17.61 |
| 15 | VO3-5740 | lo | B | 40.8 | 50.8 | 28.7 | 2.0 | 82.8 | 8.51 | 0.31 | 0.48 | 3206 | 43.85 | 17.47 |
| 10 | VO3-5730 | lo | B | 40.1 | 48.3 | 27.7 | 3.0 | 72.0 | 7.99 | 0.40 | 0.70 | 3186 | 44.97 | 16.96 |
| 2 | VO3-5714 | lo | B | 39.8 | 49.3 | 28.3 | 2.2 | 89.5 | 9.38 | 0.38 | 0.95 | 2813 | 44.42 | 17.07 |
| 17 | VO3-5744 | lo | B | 39.2 | 36.5 | 23.7 | 1.3 | 67.8 | 8.06 | 0.34 | 0.51 | 3207 | 43.62 | 19.13 |
| 18 | V99-5099 | P2 | B | 38.2 | 52.2 | 27.5 | 1.8 | 79.8 | 8.63 | 0.42 | 0.70 | 2839 | 43.32 | 16.67 |
| 34 | VO3-5778 | lo | B | 37.9 | 39.2 | 22.0 | 1.5 | 79.0 | 9.68 | 0.41 | 0.62 | 3082 | 43.16 | 17.12 |

Based on laboratory germination tests of 2004 seed, the low stachyose lines averaged 5% lower germination than high stachyose lines, but that was largely due to a few very low lines. The majority of the low stachyose lines had acceptable germinations (see Table 1). Our data indicate very weak correlations between % germination and either phytate (0.309) or sugar levels (−0.22 to 0.41) (see Table 2).

TABLE 2

| Various Trait | SUC ((%)) P.C. | SUC ((%)) P | RAF (%) P.C. | RAF (%) P | STA (%) P.C. | STA (%) P | Phytate P.C. | Phytate P |
|---|---|---|---|---|---|---|---|---|
| RAF(%) | −0.718 | 0.000 | — | | | | | |
| STA(%) | −0.814 | 0.000 | 0.957 | 0.000 | — | | | |
| Phytate | −0.865 | 0.000 | 0.851 | 0.000 | 0.882 | 0.000 | — | |
| Germ % | −0.221 | 0.160 | 0.336 | 0.030 | 0.405 | 0.008 | 0.309 | 0.047 |

Additional data collected on subsequent trials are substantially the same as the data presented above, and fully support the conclusions we have drawn (see Table 3). More specifically, Table 3 depicts more data on the exemplary soybean line V99-5089. In this table, the content of sucrose, raffinose, and stachyose, as a percent of total bean composition, are presented. As can be seen from the table, exemplary soybean line V99-5089 has exceptionally high sucrose content (approximately 1.5 times or more greater than other bean lines), and exceptionally low stachyose content (approximately 10-fold or more lower than other bean lines). These traits are heritable when the V99-5089 line is used as germ stock (e.g., Table 1 shows progeny of V99-5089).

TABLE 3

Average Sugar and Phytate Values of Parental Lines

| ID | SUC (%) | RAF (%) | STA (%) | Phytate mg/g |
|---|---|---|---|---|
| V99-5089 | 12.94 | 0.43 | 0.34 | 9.91 |
| Essex | 5.57 | 0.91 | 5.12 | 13.07 |
| Hutcheson | 5.93 | 0.75 | 4.31 | 13.38 |
| V71-370 | 6.92 | 0.90 | 3.43 | 13.28 |
| M766 | 4.07 | 0.91 | 5.33 | 11.82 |
| Mn 1401 | 4.61 | 1.23 | 4.60 | 15.90 |
| V97-7158 | 4.81 | 0.87 | 3.89 | 15.74 |
| V99-8060 | 5.11 | 0.92 | 3.85 | 16.70 |
| CX1834-1-6 | 6.80 | 0.91 | 5.78 | 8.58 |
| PI200508 | 8.2 | 1.40 | 1.0 | 17.91 |

We have identified low phytate/low stachyose lines which have germination rates equivalent to that of Essex (e.g., entries 42, 22 and 39, Table 1). As can be seen clearly, it is possible to develop soybeans with low phytate and low stachyose having normal germination. These soybeans can transmit the characteristics of low phytate, low stachyose, and high sucrose as heritable traits to progeny.

Example 4

Exemplary Strain V99-5089 is Genetically Distinct from Other Strains

V99-5089 is Distinct from CX1834-1-6

Various strains of soybean are known in the art as having seeds with low stachyose content and low phytate content. To characterize strain V99-5089 and determine its relatedness to known strains, various crosses were performed, and progeny analyzed. Results indicate that line V99-5089 is genetically distinct from other soybean lines previously characterized.

In a first series of crosses, exemplary strain V99-5089 was crossed with line CX1834-1-6, a publicly known low phytate soybean line. While this line is known to be a low phytate line, it is also known to be a high stachyose line. A total of 228 $F_{2:7}$ lines of V99-5089×CX1834-1-6 were developed for this study. The phytate content segregation of the progeny of this cross ranges from 6.9 to 18.7 mg/g, skewed toward the high peak. The bulk of the progeny population had phytate content above either of the parents of the population. This result indicates that the parental lines have recessive genes for low phytate content, and that these genes differ between the two lines. Furthermore, the low phytate genes/QTLs of CX1834-1-6 map to LG-L and LG-N as reported by Walker et al. 2006 (see above), while the low phytate gene of V99-5089 maps to LG B1 (see Table 1 and below).

V99-5089 is Distinct from LR3705 and LR4271

To further characterize the genetic loci involved in low phytate and low stachyose content of V99-5089, crosses were made between V99-5089 and the low stachyose industrial strain LR3705 and the low stachyose industrial strain LR4271, both obtained from the American Type Culture Collection. One hundred twenty seven lines were used from the cross of V99-5089 by LR3705. Among these lines, seed stachyose content varied from 0.01% to 5.26% and over 40% of the lines had less than 1% stachyose. Seed sucrose content ranged from 6.5% to 16% and raffinose content from 0.08% to 1.24%. A total of 78 samples were assayed from the cross of V99-5089 by LR4271. Stachyose content ranged from 0% to 5.42% and 25 of the lines contained less than 1% stachyose. Over 30% of the 78 samples analyzed had stachyose levels below 1%. Seed sucrose and raffinose content varied from 6.0% to 15.81% and 0.11% to 1.22%, respectively. These results indicate that the V99-5089 gene controlling sugar content is different from those of the industry lines. For example, if the lines had the same low-stachyose gene, all the progeny would be expected to have low stachyose seed. On the contrary, segregation was observed for stachyose content in both populations. This observation was further confirmed in the reciprocal crosses of both populations by testing 25 random progenies of each population.

V99-5089 is Distinct from PI200508

To yet further characterize the genetics of line V99-5089, crosses of the line were made with strain PI200508, which is an industrial strain showing low stachyose seed content. Linkage analysis and subsequent QTL analysis in a population of 55 $F_2$ individuals confirmed that there were two distinct genetic regions contributing to low stachyose in the population. This initial $F_2$ population was expanded to 96 individuals, and the linkage map was expanded to include 134 linked markers, spanning 1284 cM across all 20 linkage groups. The first low stachyose region was mapped to MLG B1, and explains 28% of the phenotypic variance. Examination of marker data revealed that it was inherited from V99-5089. This left the low stachyose region from PI 200508 undiscovered. ANOVA of early marker data indicated that the most likely location for the PI 200508 low stachyose region was on MLG C2. Marker density (and LG length) on this linkage group was doubled, and a major low-stachyose QTL, explaining a major portion of the phenotypic variance, was located near marker Satt363 on linkage group C2. Low stachyose lines in this population exhibit the PI 200508 alleles at Satt363 and Sat213, the markers flanking this QTL, suggesting that this is, in fact, the industry source of low stachyose.

To further support this conclusion, mapping was begun in two additional populations, an $F_7$ RIL, and a 138 individual $F_2$ population. These populations originate from separate crosses between V99-5089 and PI 200508. The same marker-trait associations were observed in these populations as in the original $F_2$ population. The results observed across these three experimental populations strongly suggest that the PI 200508 source of low stachyose (industry source), resides on MLG C2. Furthermore, examination of the phytate values presented in Table 3 indicate that the phytate content of these are very different. The value is 9.91 mg/g for V99-5089 and 17.91 mg/g for PI200508.

V99-5089 is Distinct from LR33

LR33 is a low stachyose soybean line (Hitz et al., 2002). To determine whether the LR33 line and the V99-5089 shared a common locus for phytate content, nucleic acid sequence analysis was performed to compare the nucleotide sequence of the locus responsible for phytate content in LR33 and the corresponding sequence in V99-5089. The analysis indicated that the mutation in LR33 is not present in the V99-5089 strain, and thus the two are distinct.

It has previously been published that the trait for low phytate content in LR33 is due to a base mutation in the D-myo-inositol 3-phosphate synthase 1 (MIPS1) gene. The mutation is reported to be a single base change from G to T at position 1,188 from the start codon. At the amino acid level, the mutation causes a change of K396 to N396 (lysine to asparagine) in the LR33 line. The myo-inositol-1-phosphate synthase mRNA sequence from soybean line Wye was submitted by Hitz et al., (2002) under GeneBank accession no. AY03802. The other MIPS1 coding sequence (from Williams 82) was deposited in GeneBank by Hegeman et al., 2001 under accession no. AF293970. According to Chappell et al., 2006 these two sequences differ by 6 nucleotides, representing two amino acid changes in the protein sequence. Chappell et al., (2006) designed primers to the ends of the MIPS1 coding sequence and amplified and sequenced the full-length gene from genomic DNA. The obtained exon sequence was identical to the Wye sequence from Hitz et al., (2002). Thus, Williams 82 and Wye have identical MIPS1 coding sequence. Also it showed that Williams 82 AF293970 sequence may not be the correct one. The complete Williams 82 MIPS1 genomic sequence has been deposited in GeneBank under accession no. DQ323904 (Chappell et al., 2006).

Using this information, the region spanning the mutation was sequenced from the LR33 line and the V99-5089 line. The following primers were used to amplify and/or sequence the region indicated below.

LEFT PRIMER:

5'-CAGCAATGCCATCCTCTATG-3' (mips1GT-F) (SEQ ID NO: 1)

RIGHT PRIMER:

5'-GAATCCTCGCATGTGTTGTG-3' (mips1GT-R) (SEQ ID NO: 2)

REGION SEQUENCE:

(SEQ ID NO: 3)
TGGATTTTATACTAATGTCATATCATTGGTGTTATTTTTACTAGCACTAT

CTATCCTTTGCATGCTTTGTTTAAAATTTATGCATTGTGCTAATTTTATA

TGGCAAAAATGGAGAAACGAGTTGATTTTTTCAAATGTTCTGTTGATGAT

TGGCAGCCAACATCTATAGTCAGTTACAACCATCTGGGAAACAATGATGG

TATGAATCTTTCGGCTCCACAAACTTTCCGTTCCAAGGAAATCTCCAAGA

GCAACGTTGTTGATGATATGGTCAACAGCAATGCCATCCTCTATGAGCCT

GGTGAACATCCAGACCATGTTGTTGTTATTAAGGTAAATTTTGTTTCACC

CATTTTTCTGTTTCTTTCTCTTGTCAGGGCTTTGATTATTCTATCTGCTT

TGTTGCCTTTGCAGTATGTGCCTTACGTAGGGGACAGCAAGAGAGCCATG

GATGAGTACACTTCAGAGATATTCATGGGTGGAAAGAGCACCATTGTTTT

GCACAACACATGCGAGGATTCCCTCTTAGCTGCTCCTATTATCTTGGACT

TGGTCCTTCTTGCTGAGCTCAGCACTAGAATCGAGTTTAAAGCTGAAAAT

GAGGTCTGTATGCATTGCTAAATAATTTCATTGCTTGATTGTATTAGTCA

TTGTATTTTTTTCAGCCTTCTGAGGTCACTATGTTGTGGTGATTGCTGCA

GGGAAAATTCCACTCATTCCACCCAGTTGCTACCATCCTCAGCTACCTCA

CCAAGGCTCCTCTGGTGAGTTTAATCTAAT

A comparison of the sequences of the two is presented in Table 4, below. As can be seen from the Table, the V99-5089 sequence does not contain the G to T mutation of the LR33 line, but rather includes the wild-type base at this position. Accordingly, the phenotype of low phytate content for the two lines is due to different genetic causes.

TABLE 4

Comparison of Nucleotide Sequences

LR33: 5'-AGGGGACAGCAATAGAGCCATGGAT-3' (SEQ ID NO: 4)

V99-5089: 5'-AGGGGACAGCAAGAGAGCCATGGAT-3' (SEQ ID NO: 5)

Further analysis of this region of the genomes of LR33 and V99-5089 indicated other differences. For example, the V99-5089 region contained a unique SNP-type difference between V99-5089 and other lines, including Williams 82 and LR33. As shown in Table 5, the V99-5089 line contains a C to G conversion in this region, resulting in a His to Asp conversion in the encoded protein.

TABLE 5

Comparison of Nucleotide and Amino Acid Sequences

A:

| Williams/LR33: | 5'-CCTGGTGAACATCCAGACCATG-3' | (SEQ ID NO: 6) |
| V99-5089: | 5'-CCTGGTGAACATCCAGACGATG-3' | (SEQ ID NO: 7) |

B:

| Williams/LR33: | PGEHPDHVVVIKV | (SEQ ID NO: 8) |
| V99-5089: | PGEHPDDVVVIKV | (SEQ ID NO: 9) |

A deposit intended to meet all requirements of 37 CFR §§ 1.801-1.809 of at least 2,500 seeds of the proprietary Soybean Cultivar V99-5 089 disclosed above and recited in the appended claims was made by Dr. Saghai Maroof under the provisions of the Budapest Treaty with the American Type Culture Collection (ATCC), 10801 University Boulevard, Manassas, Va. 20110 on May 9, 2011. The deposit was assigned ATCC Accession Number PTA-1187. This deposit will be maintained in the depository for a period of thirty years, or five years after the last request, or for the enforceable life of the patent, whichever is longer. Should the deposited seeds become non-viable, the deposit will be replaced upon request. The seeds will be irrevocable, and without restriction or condition released to the public upon the issuance of a patent.

Sequence alignment and analysis of the partial sequence of MIPS1 from V99-5089 clearly showed that this line is different from LR33. These differences were revealed at two levels: nucleotide and corresponding amino acids. Also we have mapped MIPS1 gene 3.8 cM above Satt453 SSR marker on soybean linkage group B1. Mapping data were collected from 192 individuals of F2 V995089× Essex segregating population. Up to four sets of quantitative trait data were collected for this population from two field (Blacksburg, Va. and Warsaw, Va.) and two greenhouse experiments. The trait data included sucrose, raffinose, stachyose and phytate values. For genome-wide scanning of marker-phenotype associations, segregation data for 92 markers were also collected. Data analysis indicated the existence of very strong marker genotype associations with sugar and phytate phenotypic variation on LG-B1 within MIPS1-Sat331 interval. Therefore, the LG-B1 region positioned between the map interval 58 and 64 cM is the location of major QTL/QTLs for sucrose, stachyose, and phytate content in V995089.

MIPS is a highly conserved enzyme and plays key role in phytic acid biosynthesis. It was shown that MIPS family consists of four genes (Chappell et al., 2006). To determine whether these genes have a genetic association with lpa related and other QTLs, we have mapped all four genes by using four mapping populations. MIPS1 gene was mapped on LG-B1 in two populations CX1834-1-6×V99-3337 and V99-5089× Essex consisting of 207 and 192 F2 individuals, respectively. Data obtained showed that MIPS1 and Satt453 are located in the region of a major QTL controlling phytate content on linkage group B1 in V99-5089. MIPS2 was mapped on top of LG-G (2 cM above Satt038) in two populations: CX1834-1-6×V99-3337 (already mentioned above)

and V99-5089×PI200508 (which consisted of 76 F2 individuals). MIPS3 was mapped on LG-A1 9 cM below Satt619 based on data obtained from 207 RILs of V71-370× PI407162. Map position of the MIPS4 gene (4 cM below Satt424 on LG-A2) was determined in F2 population of V995089× Essex with 94 individuals. Therefore, phytate QTL of V99-5089 is located on a different linkage group than those for MIPS2, 3, and 4.

It will be apparent to those skilled in the art that various modifications and variations can be made in the practice of the present invention without departing from the scope or spirit of the invention. Other embodiments of the invention will be apparent to those skilled in the art from consideration of the specification and practice of the invention. It is intended that the specification and examples be considered as exemplary only.

REFERENCES

All references cited herein are incorporated herein in their entireties by reference. The following references are listed by way of example, and are specifically incorporated herein by reference.

Chappell, A. S. et al., *Plant Breeding* 125:493-500, 2006.
Gao, Y. et al., *Crop Sci.* 47:1797-1803, 2007.
Hegeman, C. E. et al., *Plant Physiology* 125:1941-1948, 2001.
Hitz, W. D. et al., *Plant Physiology* 128:650-660, 2002.
Walker, D. R. et al., *Crop Sci.* 45:390-397, 2006.
Wilcox, J. R. et al., *Crop Sci.* 40:1601-1605, 2000.
Yuan, F.-J. et al., *Theor. Appl. Genet.* 115:945-957, 2007.

The invention claimed is:

1. A method of improving the nutritional value of a food containing soybeans or soybean products, said method comprising:

making a food containing soybean or a product of soybean, wherein the soybean is line V99-5089 or progeny thereof, wherein the method increases the amount of digestible phosphorus and carbohydrates available to the consumer of the food, as compared to food containing soybeans or soybean products that are not from soybean line V99-5089, seeds of said soybean line V99-5089 having been deposited under ATCC Accession No. PTA-1187.

2. The method of claim 1, wherein the method is a method of making a food for an agricultural animal, a domesticated animal, a companion animal, or a human.

3. The method of claim 1, wherein the method does not comprise adding phytase or inorganic phosphorus to the food.

4. A plant or seed of soybean line V99-5089, seeds of said soybean line V99-5089 having been deposited under ATCC Accession No. PTA-1187.

5. F1 progeny of a cross between any plant and the plant of claim 4, or a cross between soybean line V99-5089 and itself.

6. Progeny of, or plant derived from, the plant of claim 4 comprising the mutant mips1 gene of soybean line V99-5089, seeds of said soybean line V99-5089 having been deposited under ATCC Accession No. PTA-1187.

7. The progeny or plant of claim 6, wherein seeds of which comprise less than or equal to 1% stachyose content by dry weight and less than or equal to 13 mg of phytic acid per gram of seed by dry weight.

8. The progeny or plant of claim 7, seeds of which comprise greater than or equal to 7% sucrose by dry weight.

9. A soybean, or soybean food product comprising soybeans or products, from the soybean line or seed of claim 4, or progeny thereof, wheren said progeny comprise the mutant mips1 gene of soybean line V99-5089, and wherein said food product comprises DNA of said plant, seed, or progeny.

10. The soybean or food product of claim 9, which is animal feed.

11. The soybean or food product of claim 9, which is food for humans.

12. The food product of claim 10, which is animal feed for an agricultural or a domesticated animal or a companion animal.

13. A method of producing a soybean plant or seed, comprising crossing a plant of soybean line V99-5089 with itself or any soybean plant, seeds of said soybean line V99-5089 having been deposited under ATCC Accession No. PTA-1187.

14. The method of claim 13 comprising genetic engineering techniques.

15. The method of claim 13 comprising producing a soybean plant or seed, wherein the seed or seeds of the plant comprise less than or equal to 1% stachyose content by dry weight and less than or equal to 13 mg of phytic acid per gram of seed by dry weight.

16. The method of claim 15 comprising producing a soybean plant or seed, wherein the seed or seeds of the plant comprise greater than or equal to 7% sucrose by dry weight.

* * * * *

UNITED STATES PATENT AND TRADEMARK OFFICE
CERTIFICATE OF CORRECTION

PATENT NO. : 8,003,856 B2  
APPLICATION NO. : 12/033830  
DATED : August 23, 2011  
INVENTOR(S) : Mohammad A. Saghai Maroof and Glenn R. Buss Page 1 of 1

It is certified that error appears in the above-identified patent and that said Letters Patent is hereby corrected as shown below:

"ATCC Accession No. PTA-1187" should be changed to "ATCC Accession No. PTA-11874" throughout the patent and specifically at the following locations:

In The Specification  
Col. 18, Line 28

In The Claims  
Col. 21 Claim 1, Line 67  
Col. 22 Claim 4, Line 61  
Col. 22 Claim 6, Line 67  
Col. 24 Claim 13, Line 5

Signed and Sealed this  
Eighteenth Day of October, 2011

David J. Kappos  
*Director of the United States Patent and Trademark Office*